(12) United States Patent
Eisinger et al.

(10) Patent No.: US 11,534,164 B2
(45) Date of Patent: Dec. 27, 2022

(54) STRAIN GAUGE STABILIZATION IN A SURGICAL DEVICE

(71) Applicant: Covidien LP, Mansfield, MA (US)

(72) Inventors: Joseph Eisinger, Northford, CT (US); David Valentine, Jr., Hamden, CT (US); Scott Firth, Guilford, CT (US)

(73) Assignee: Covidien LP, Mansfield, MA (US)

( * ) Notice: Subject to any disclaimer, the term of this patent is extended or adjusted under 35 U.S.C. 154(b) by 386 days.

(21) Appl. No.: 16/808,561

(22) Filed: Mar. 4, 2020

(65) Prior Publication Data

US 2020/0315623 A1 Oct. 8, 2020

Related U.S. Application Data

(60) Provisional application No. 62/829,698, filed on Apr. 5, 2019.

(51) Int. Cl.
*A61B 17/072* (2006.01)
*A61B 17/00* (2006.01)

(52) U.S. Cl.
CPC ............ *A61B 17/07207* (2013.01); *A61B 2017/00084* (2013.01); *A61B 2017/00473* (2013.01);
(Continued)

(58) Field of Classification Search
CPC .............. A61B 17/07207; G01K 7/023; G01L 5/1627; G01L 5/0028; H01M 6/5044
See application file for complete search history.

(56) References Cited

U.S. PATENT DOCUMENTS 3,193,165 A  7/1965  Akhalaya et al.
3,388,847 A  6/1968  Kasulin et al.
(Continued)

FOREIGN PATENT DOCUMENTS

CA  908529 A  8/1972
CA  2805365 A1  8/2013
(Continued)

OTHER PUBLICATIONS

Extended European Search Report issued in corresponding Application No. EP 20167963.6 dated Oct. 1, 2020 (8 pages).
(Continued)

*Primary Examiner* — Nathaniel C Chukwurah
(74) *Attorney, Agent, or Firm* — Carter, DeLuca & Farrell LLP

(57) ABSTRACT

A surgical device includes an adapter assembly including a tubular housing having a proximal end portion configured to couple to a handle assembly, and a load sensing assembly disposed with the tubular housing. The load sensing assembly is configured to measure a load exerted on the tubular housing and includes: a sensor body including a pocket defined therein; a load sensor circuit disposed within the pocket and coupled to the sensor body; a signal processing circuit disposed within the pocket and electrically coupled to the load sensor circuit; a cover defining a cavity and disposed over the pocket and enclosing the load sensor circuit and the signal processing circuit therein, the cover being coupled to the sensor body thereby forming a first hermetic seal therebetween; and a thermal management material disposed within the cavity and in contact with the load sensor circuit and the signal processing circuit.

20 Claims, 14 Drawing Sheets

(52) U.S. Cl.
CPC .......... *A61B 2017/00486* (2013.01); *A61B 2017/00831* (2013.01); *A61B 2017/07271* (2013.01); *A61B 2562/0252* (2013.01); *A61B 2562/0261* (2013.01); *A61B 2562/0271* (2013.01)

(56) References Cited

U.S. PATENT DOCUMENTS

| | | |
|---|---|---|
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |

(56) References Cited

U.S. PATENT DOCUMENTS

| | | |
|---|---|---|
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,464,600 B2 * | 12/2008 | Kurtz .................... G01K 7/023 374/E7.018 |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |

(56) References Cited

U.S. PATENT DOCUMENTS

| | | |
|---|---|---|
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 2003/0111507 A1 | 6/2003 | Nunez |
| 2004/0073090 A1 | 4/2004 | Butler et al. |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2011/0257636 A1 | 10/2011 | Whitman et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |

(56) References Cited

U.S. PATENT DOCUMENTS

| | | |
|---|---|---|
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2014/0190275 A1* | 7/2014 | McIlravey ............ G01L 5/1627 73/862.29 |
| 2015/0374371 A1 | 12/2015 | Richard et al. |
| 2016/0143641 A1 | 5/2016 | Sapienza et al. |
| 2016/0157856 A1 | 6/2016 | Williams et al. |
| 2016/0174988 A1 | 6/2016 | D'Agostino et al. |
| 2016/0302792 A1 | 10/2016 | Motai |
| 2017/0202605 A1* | 7/2017 | Shelton, IV ........ H01M 6/5044 |
| 2018/0042610 A1* | 2/2018 | Sgroi, Jr. ............ G01L 5/0028 |

FOREIGN PATENT DOCUMENTS

| | | |
|---|---|---|
| CN | 103 622 727 A | 3/2014 |
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 2684529 A2 | 1/2014 |
| EP | 2954854 A2 | 12/2015 |
| EP | 3231374 A1 | 10/2017 |
| EP | 3284416 A1 | 2/2018 |
| EP | 3318212 A1 | 5/2018 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| GB | 2317745 A | 4/1998 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 2008107918 A1 | 9/2008 |
| WO | 2016171947 A1 | 10/2016 |

OTHER PUBLICATIONS

Detemple, P., "Microtechnology in Modern Health Care", Med Device Technol. 9(9):18-25 (1998).

Abridged Data Sheet, "DeepCover Secure Authenticator with 1-Wire SHA-256 and 512-Bit User EEPROM", Maxim Integrated Products, Inc. pp. 1-4;42; Dec. 2012.

Data Sheet "DS28E15-1—Sire SHA-256 Secure Authenticator with 512-Bit User EEPROM"; IC-On-Line, Electronic Component Manufacturers, pp. 1-2; Aug. 2013.

* cited by examiner

STRAIN GAUGE STABILIZATION IN A SURGICAL DEVICE

CROSS-REFERENCE TO RELATED APPLICATIONS

This application claims the benefit of and priority to U.S. Provisional Patent Application Ser. No. 62/829,698 filed Apr. 5, 2019, the entire disclosure of which is incorporated by reference herein.

BACKGROUND

1. Technical Field

The present disclosure relates to surgical devices. More specifically, the present disclosure relates to handheld electromechanical surgical systems for performing surgical procedures having reusable components with load sensing devices.

2. Background of Related Art

One type of surgical device is a circular clamping, cutting and stapling device. Such a device may be employed in a surgical procedure to reattach rectum portions that were previously transected, or similar procedures. Conventional circular clamping, cutting, and stapling devices include a pistol or linear grip-styled structure having an elongated shaft extending therefrom and a staple cartridge supported on the distal end of the elongated shaft. In this instance, a physician may insert the loading unit portion of the circular stapling device into a rectum of a patient and maneuver the device up the colonic tract of the patient toward the transected rectum portions. The loading unit includes a cartridge assembly having a plurality of staples. Along the proximal portion of the transected colon, an anvil assembly can be purse-stringed therein. Alternatively, if desired, the anvil portion can be inserted into the colon through an incision proximal to the transected colon. The anvil and cartridge assemblies are approximated toward one another and staples are ejected from the cartridge assembly toward the anvil assembly thereby forming the staples in tissue to affect an end-to-end anastomosis, and an annular knife is fired to core a portion of the clamped tissue portions. After the end-to-end anastomosis affected, the circular stapling device is removed from the surgical site.

A number of surgical device manufacturers have also developed proprietary powered drive systems for operating and/or manipulating the end effectors. The powered drive systems may include a powered handle assembly, which may be reusable, and a disposable end effector that is removably connected to the powered handle assembly.

Many of the existing end effectors for use with existing powered surgical devices and/or handle assemblies are driven by a linear driving force. For example, end effectors for performing endo-gastrointestinal anastomosis procedures, end-to-end anastomosis procedures and transverse anastomosis procedures, are actuated by a linear driving force. As such, these end effectors are not compatible with surgical devices and/or handle assemblies that use rotary motion.

In order to make the linear driven end effectors compatible with powered surgical devices that use a rotary motion to deliver power, a need exists for adapters to interconnect the linear driven end effectors with the powered rotary driven surgical devices. These adapters may also be reusable, and as such, need to able to withstand multiple sterilization cycles. As these adapters are becoming more sophisticated and include various electronic components, there is a need for electronic components disposed within the adapters that can withstand multiple autoclave cycles.

SUMMARY

Powered surgical devices may include various sensors for providing feedback during their operation. However, one limitation of the electronics and sensors used in the sterile environment of the operating room is that they need to be designed to withstand multiple cleaning and autoclave cycles. In order to gather information of the mechanical forces applied by the powered surgical devices, load sensing devices, such as load cells, are disposed on one or more mechanical components of the powered surgical device and/or adapters coupled thereto.

Load sensing devices are also coupled to signal processing and conditioning circuit that are separately packaged from the load sensing devices. These circuits process the change in resistance of the load sensing devices and determine the load applied thereto. In particular, components of signal processing circuits are usually disposed on printed circuit boards ("PCB") housed with other electronic and electric components of powered surgical devices. Remote placements of these circuit components away from the load sensing devices is due to their size and shape, which prevent the PCB from being in close proximity to the load sensing devices. Accordingly, these circuits are connected to the load sensing devices through wired connections, which involve longer leads (e.g., flexible printed circuit traces over 10 centimeters) for transmitting analog signals from the load sensing devices to the signal processing circuit. Longer wired connections can result in signal loss and also increase the chances of failure due to exposure of these leads to disinfecting and sterilization cycles. Harsh environments from disinfecting solutions and residual moisture from the autoclaving processes breaks down the components and coatings in flex circuits, thereby causing signal degradation. Further, in surgical devices where saline irrigation is utilized, the saline can further breakdown of mechanical integrity of these circuits resulting in signal degradation.

In addition, the separation between the load sensing devices and the signal processing circuitry also affects fidelity of analog sense signals transmitted from the load sensing devices. The analog voltage signals are low voltage signals and are therefore more susceptible to interference of the load measured by the load sensing devices due to water ingress in the PCB, solder connections, and/or traces, small contamination including solder flux and autoclave mineral deposits, as well as radio frequency interference due to long conductor travel length. Remote placement of signal processing circuits also results in lower bit resolution. Furthermore, conventional signal processing circuits used with load sensing devices have no ability to compensate for zero balance fluctuations in load sensing devices due to inconsistencies of sensor bodies housing the load sensing devices (e.g., during manufacture and assembly of the sensors). As used herein, the term "zero balance" denotes a baseline signal from a load sensing device corresponding to a condition in which the load sensing device is unloaded.

The present disclosure provides for a combined load sensing assembly having one or more load sensing devices and a signal processing circuit disposed within a hermetically sealed housing of the sensor. This obviates the problem of transmitting analog load sensing signals along long leads and protects the load sensing devices and the signal processing circuit from exposure to elements including sterilization cycles (e.g., autoclaving). In addition, the signal processing circuit is programmable to optimize the sensor signals by adjusting gain and offset values of sensor signals.

Conventional load sensing devices that utilize strain gauge technology typically suffer from the lack of adjustability or tuning of the load sensing devices. In particular, variations in the load sensing devices, tolerances in sensor bodies, placement of the load sensing devices, and other factors, contribute to zero balance variations, which result in variable zero balance values across the lot of load sensing devices. Unfortunately, in conventional load sensing devices zero balance cannot be adjusted for each individual load sensing device. The present disclosure provides a signal processing circuit that may be programmed to adjust zero balance after the load sensor is manufactures and/or assembled.

The present disclosure also provides a novel design for housing a load sensing device to limit thermal fluctuations in sensitivity and accuracy of these load sensing devices, such as strain gauges. More specifically, due to the sensitivity of strain gauges, any change in temperature, which in turn affects electrical conductivity of the strain gauge or the signal processing circuit can introduce errors in the measurement signal. This can be especially problematic because the signal processing circuit and the strain gauge generate heat when operated due to transmission of electrical signals therethrough.

To deal with heat transfer, the present disclosure uses a fluid, gel, or other electrically non-conductive, but thermally conducive material to maintain stable temperatures of the strain gauge. The present disclosure fills a cavity defined by a cover, which houses the strain gauge and the signal processing circuit, with a heat transferring composition. Due to additional heat transfer, this allows the signal processing circuit to be packaged in close proximity with the strain gauge, and for the heat generated by the signal processing circuit to be efficiently dissipated, which in turn, minimizes strain gauge error. Conventional configurations do not place the strain gauge in close thermal proximity to the signal processing circuit, so that heat produced by the signal processing circuit does not affect the temperature of the strain gauge. However, due to the novel design of placing the strain gauge within the same housing as the signal processing circuit, the present disclosure provides a solution to the additional heat being generated due to this configuration.

According to one embodiment of the present disclosure, a load sensing assembly includes: a sensor body including a pocket defined therein and a load sensor circuit disposed within the pocket and coupled to the sensor body. The load sensing assembly also includes a signal processing circuit disposed within the pocket and electrically coupled to the load sensor circuit; a cover defining a cavity and disposed over the pocket and enclosing the load sensor circuit and the signal processing circuit therein, the cover being coupled to the sensor body thereby forming a first hermetic seal therebetween; and a thermal management material disposed within the cavity and in contact with the load sensor circuit and the signal processing circuit.

According to another embodiment of the present disclosure, an adapter assembly includes a tubular housing having a proximal end portion and a distal end portion and a load sensing assembly disposed with the tubular housing. The load sensing assembly is configured to measure a load exerted on the tubular housing. The load sensing assembly includes a sensor body including a pocket defined therein and a load sensor circuit disposed within the pocket and coupled to the sensor body. The load sensing assembly also includes a signal processing circuit disposed within the pocket and electrically coupled to the load sensor circuit; a cover defining a cavity and disposed over the pocket and enclosing the load sensor circuit and the signal processing circuit therein, the cover being coupled to the sensor body thereby forming a first hermetic seal therebetween; and a thermal management material disposed within the cavity and in contact with the load sensor circuit and the signal processing circuit.

According to a further embodiment of the present disclosure, a surgical device includes: a handle assembly including a controller and an adapter assembly including a tubular housing having a proximal end portion configured to couple to the handle assembly and a distal end portion. The surgical device also includes a load sensing assembly disposed with the tubular housing. The load sensing assembly is configured to measure a load exerted on the tubular housing. The load sensing assembly includes a sensor body including a pocket defined therein and a load sensor circuit disposed within the pocket and coupled to the sensor body. The load sensing assembly also includes a signal processing circuit disposed within the pocket and electrically coupled to the load sensor circuit; a cover defining a cavity and disposed over the pocket and enclosing the load sensor circuit and the signal processing circuit therein, the cover being coupled to the sensor body thereby forming a first hermetic seal therebetween; and a thermal management material disposed within the cavity and in contact with the load sensor circuit and the signal processing circuit. The surgical device further includes a surgical end effector configured to couple to the distal end portion of the adapter assembly.

According to one aspect of any of the above embodiments, the sensor body further includes a slot defined therein, the slot being connected to the pocket. The load sensing assembly also includes a header having at least one pin coupled to the load sensor circuit and the signal processing circuit, wherein the header is coupled to the sensor body thereby forming a second hermetic seal therebetween.

According to another aspect of any of the above embodiments, the load sensor circuit includes at least one load sensing device. The signal processing circuit includes a flexible circuit board having a dielectric wrap disposed over the flexible circuit board.

According to a further aspect of any of the above embodiments, the thermal management material includes a grease component. The grease component is selected from the group consisting of a mineral oil, a petroleum oil, and a synthetic oil. The thermal management material may also include a filler component. The filler component may be one of metal particles, metal oxide particles, metal nitride particles, metal carbide particles, metal diboride particles, graphite particles, and combinations thereof. The thermal management material may further include a fusible metal component having a first phase at a first temperature and a second phase at a second temperature, which is higher than the first temperature. The fusible metal component may include metal particles selected from the group consisting of bismuth, tin, lead, cadmium, and indium.

BRIEF DESCRIPTION OF THE DRAWINGS

Embodiments of the present disclosure are described herein with reference to the accompanying drawings, wherein.

DETAILED DESCRIPTION OF EMBODIMENTS

Figure 1:
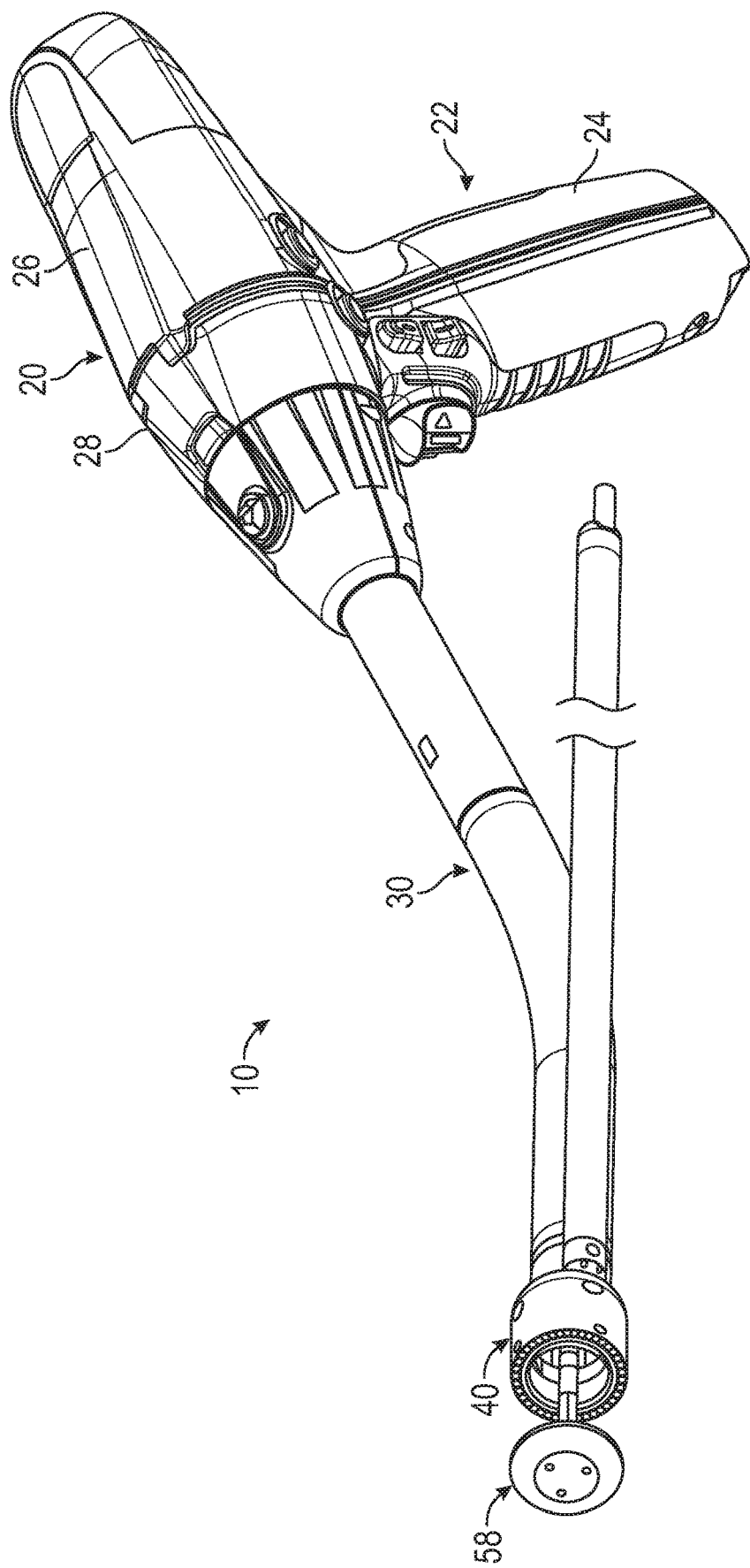
FIG. 1 is a perspective view of a handheld surgical device, an adapter assembly, an end effector having a reload and an anvil assembly according to an embodiment of the present disclosure.

Embodiments of the present disclosure are now described in detail with reference to the drawings in which like reference numerals designate identical or corresponding elements in each of the several views. As used herein, the term "clinician" refers to a doctor, a nurse or any other care provider and may include support personnel. Throughout this description, the term "proximal" will refer to the portion of the device or component thereof that is closer to the clinician and the term "distal" will refer to the portion of the device or component thereof that is farther from the clinician. Additionally, in the drawings and in the description that follows, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

The present disclosure relates to powered surgical devices having electronic sensors for monitoring mechanical strain and forces imparted on components of the powered surgical devices. More particularly, this disclosure relates to load measuring sensors including load sensing devices as well as analog and digital circuitry that are hermetically sealed such that the load sensors are configured to resist harsh environments. In the event that electrical connections of the powered surgical devices are compromised during use, measurement signals output by the sensors of the present disclosure remain unaltered. In addition, the sensors are programmable allowing for adjustments to gain and offset values in order to optimize the measurement signals.

With reference to FIG. 1, a powered surgical device 10 includes a handle assembly 20, which is configured for selective connection with an adapter assembly 30, which in turn, is configured for selective connection with an end effector, such as an annular reload 40. Although generally referred to as being a powered surgical device, it is contemplated that the surgical device 10 may be a manually actuated and may include various configurations.

Figure 2:
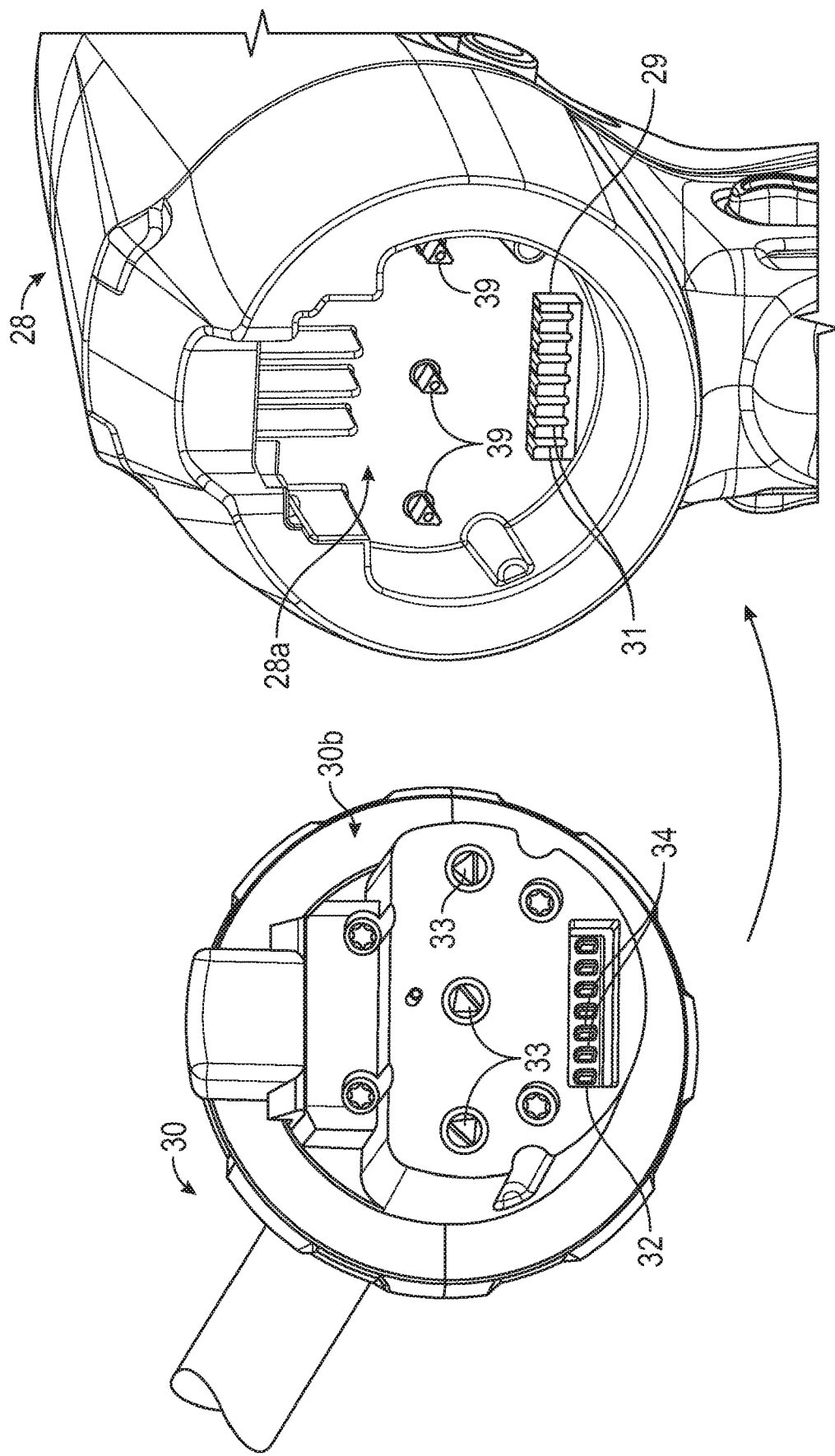
FIG. 2 is a perspective view illustrating a connection of the adapter assembly and the handle assembly of FIG. 1 according to an embodiment of the present disclosure.

The handle assembly 20 includes a handle housing 22 having a lower housing portion 24, an intermediate housing portion 26 extending from and/or supported on a portion of the lower housing portion 24, and an upper housing portion 28 extending from and/or supported on a portion of the intermediate housing portion 26. As shown in FIG. 2, a distal portion of the upper housing portion 28 defines a nose or connecting portion 28a that is configured to accept a proximal end portion 30b of the adapter assembly 30.

Figure 3:
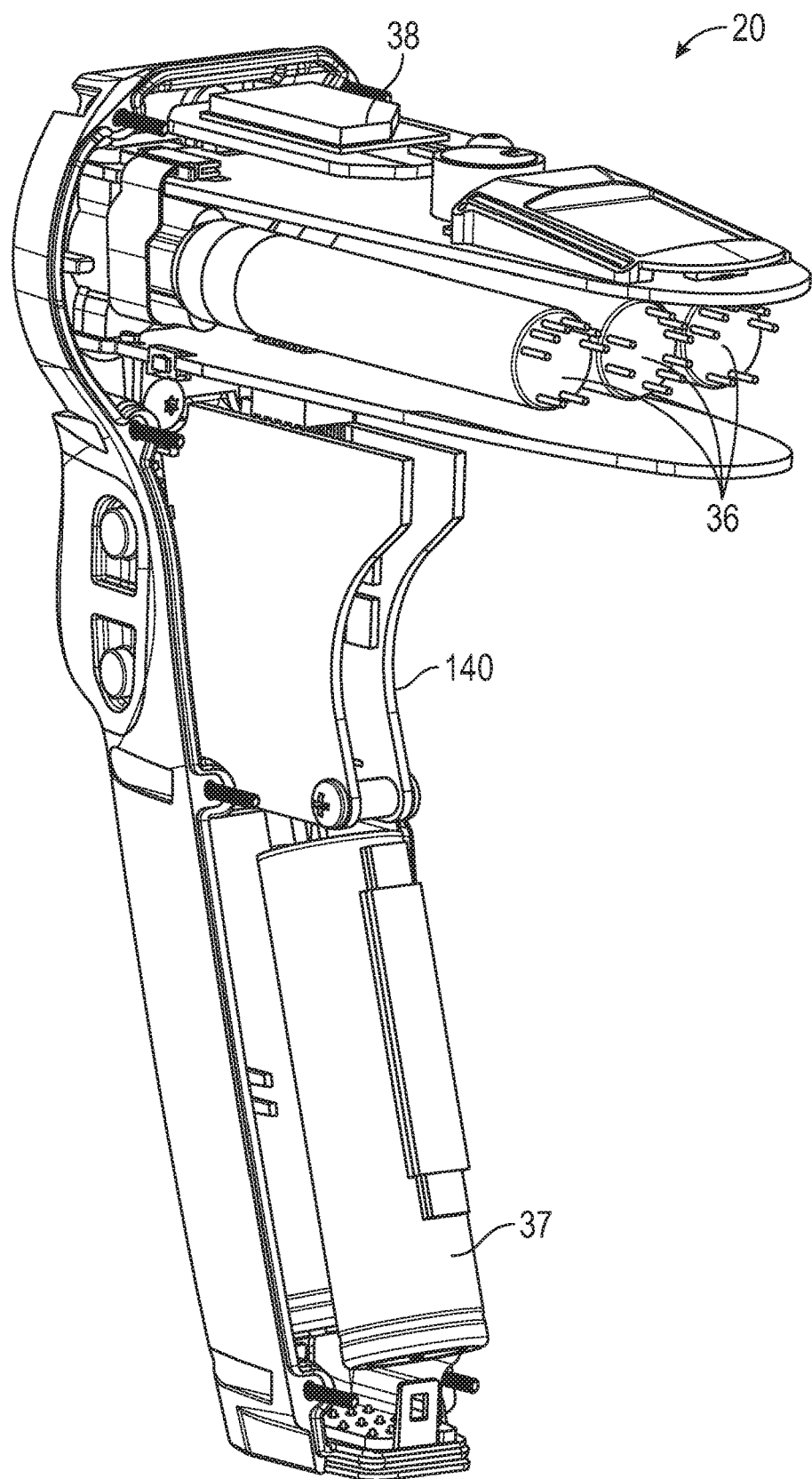
FIG. 3 is perspective view of internal components of the handle assembly according to an embodiment of the present disclosure.

With reference to FIG. 3, the handle assembly 20 includes one or more motors 36 which are coupled to a battery 37. The handle assembly 20 also includes a main controller 38 for operating the motors 36 and other electronic components of the handle assembly 20, the adapter assembly 30, and the reload 40. The motors 36 are coupled to corresponding drive shafts 39 (FIG. 2), which are configured to engage sockets 33 on the proximal end portion 30b, such that rotation of the drive shafts 39 is imparted on the sockets 33. The actuation assembly 52 (FIG. 6B) is coupled to a respective socket 33. The actuation assembly 52 is configured to transfer rotational motion of the sockets 33 into linear motion and to actuate the reload 40 (FIG. 1) along with the anvil assembly 58.

Figure 4:
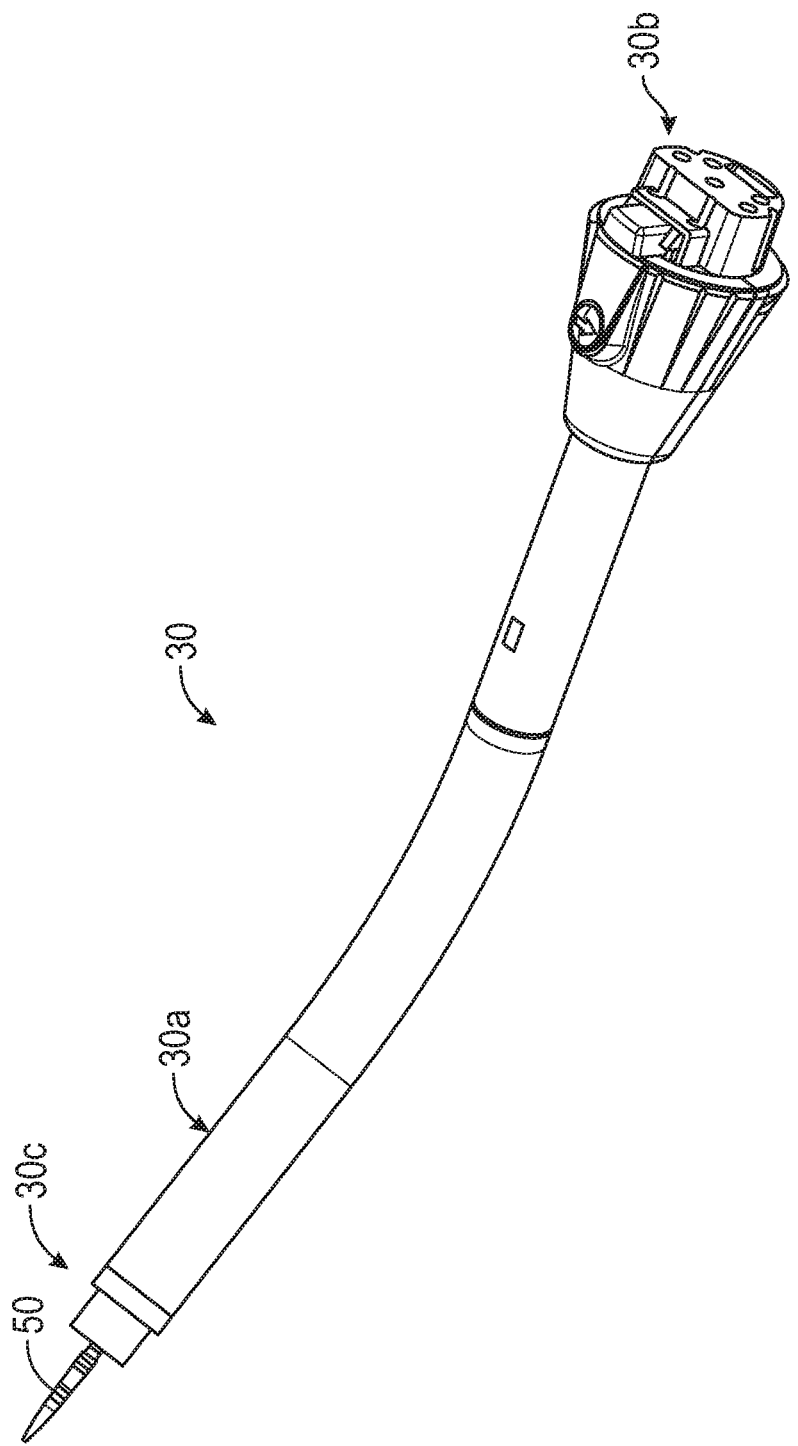
FIG. 4 is a perspective view of the adapter assembly of FIG. 1 without the reload according to an embodiment of the present disclosure.

With reference to FIG. 4, the adapter assembly 30 includes a tubular housing 30a that extends between a proximal end portion 30b that is configured for operable connection to the connecting portion 28a of the handle assembly 20 and an opposite, distal end portion 30c that is configured for operable connection to the reload 40. In this manner, the adapter assembly 30 is configured to convert a rotational motion provided by the handle assembly 20 into axial translation useful for advancing/retracting a trocar member 50 slidably disposed within the distal end portion 30c of the adapter assembly 30 (FIG. 5) for firing staples of the reload 40.

With reference to FIG. 2, the connecting portion 28a includes an electrical receptacle 29 having a plurality of electrical contacts 31, which are in electrical communication with electronic (e.g., main controller 38) and electrical components (e.g., battery 37) of the handle assembly 20. The adapter assembly 30 includes a counterpart electrical connector 32 that is configured to engage the electrical receptacle 29. The electrical connector 32 also includes a plurality of electrical contacts 34 that engage and electrically connect to their counterpart electrical contacts 31.

With reference to FIG. 4, the trocar member 50 is slidably disposed within the tubular housing 30a of the adapter assembly 30 and extends past the distal end portion 30c thereof. In this manner, the trocar member 50 is configured for axial translation, which in turn, causes a corresponding axial translation of an anvil assembly 58 (FIG. 1) of the reload 40 to fire the staples (not shown) disposed therein. The trocar member 50 includes a proximal end which is coupled to the tubular housing 30a of the adapter assembly 30. A distal end portion of the trocar member 50 is configured to selectively engage the anvil assembly 58 of the reload 40 (FIG. 4). In this manner, when the anvil assembly 58 is connected to the trocar member 50, as will be described in detail hereinbelow, axial translation of the trocar member 50 in the first direction results in an opening of the anvil assembly 58 relative to the reload 40, and axial translation of the trocar member 50 in a second, opposite direction, results in a closing of the anvil assembly 58 relative to the reload 40.

Figure 5:
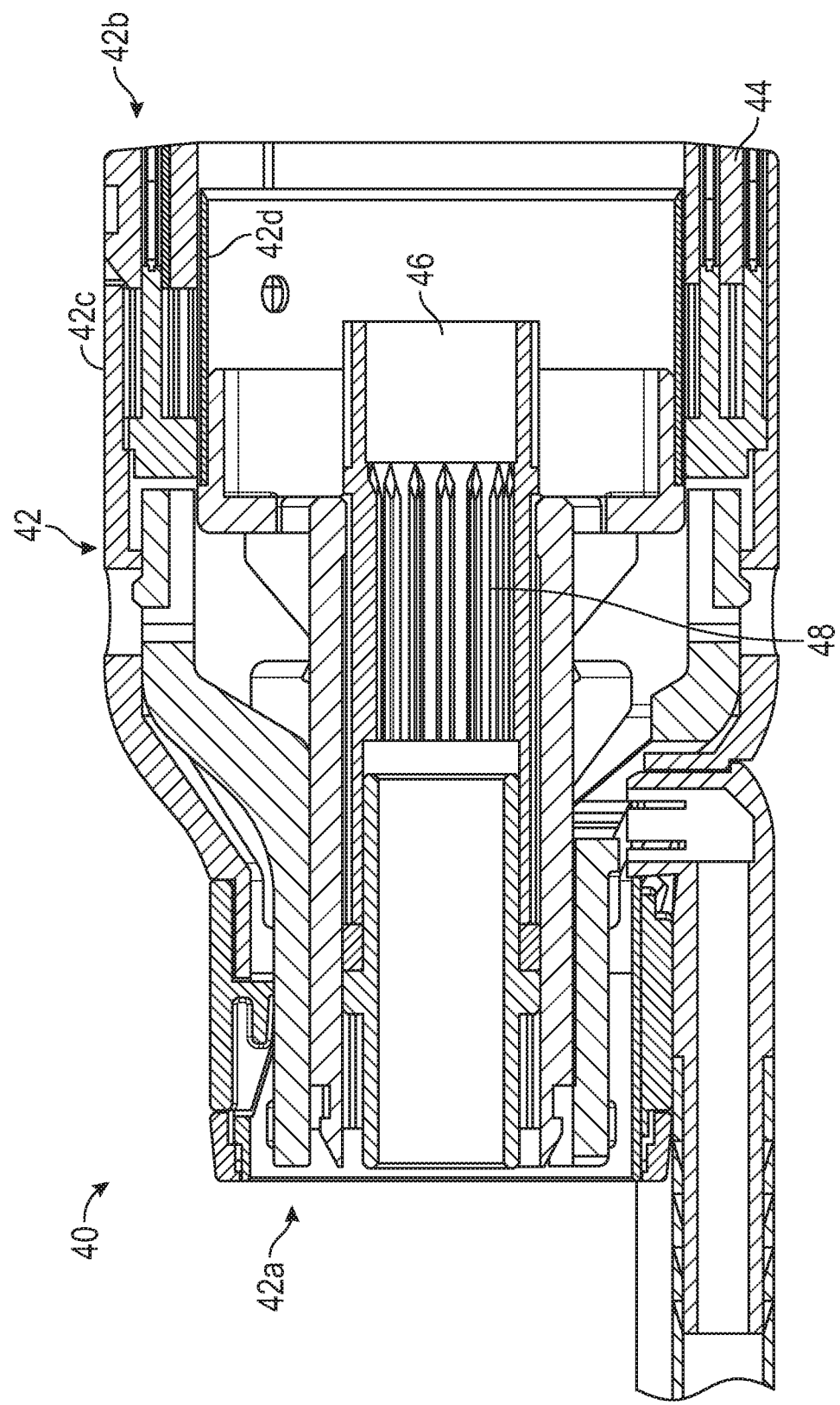
FIG. 5 is a side, cross-sectional view, of the reload of FIG. 1 according to an embodiment of the present disclosure.

As illustrated in FIGS. 1 and 5, the reload 40 is configured for operable connection to adapter assembly 30 and is configured to fire and form an annular array of surgical staples, and to sever a ring of tissue. The reload 40 includes a housing 42 having a proximal end portion 42a and a distal end portion 42b and a staple cartridge 44 fixedly secured to the distal end portion 42b of the housing 42. The proximal end portion 42a of the housing 42 is configured for selective connection to the distal end portion 30c of the adapter assembly 30 and includes a means for ensuring the reload 40 is radially aligned or clocked relative to the adapter assembly 30.

With reference to FIG. 5, the housing 42 of the reload 40 includes an outer cylindrical portion 42c and an inner cylindrical portion 42d. The outer cylindrical portion 42c and the inner cylindrical portion 42d of the reload 40 are coaxial and define a recess 46. The recess 46 of the reload 40 includes a plurality of longitudinally extending ridges or splines 48 projecting from an inner surface thereof which is configured to radially align the anvil assembly 58 relative to the reload 40 during a stapling procedure.

Figure 6A:
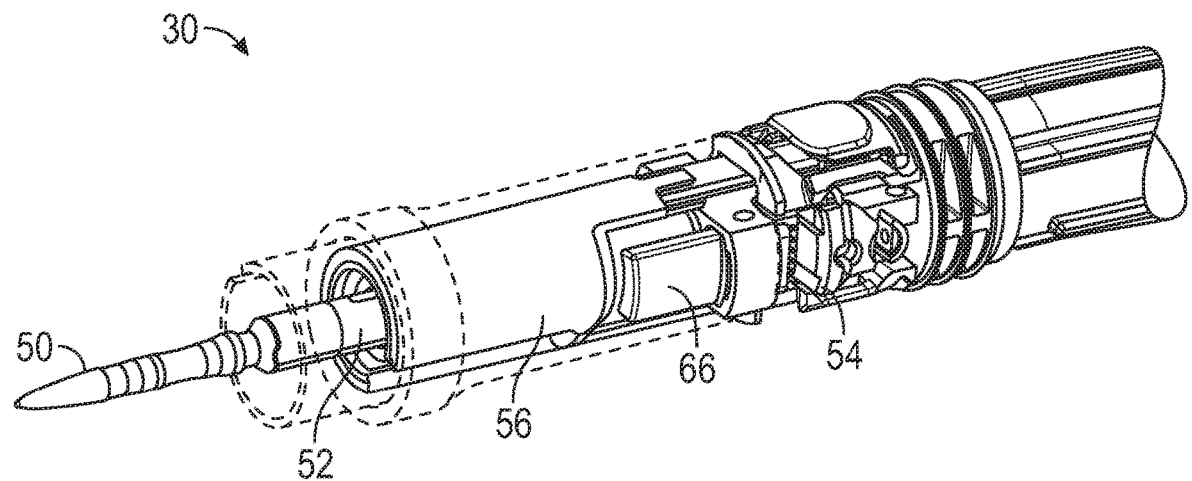
FIG. 6A is a perspective view of the distal end portion of the adapter assembly according to an embodiment of the present disclosure.
Figure 6B:
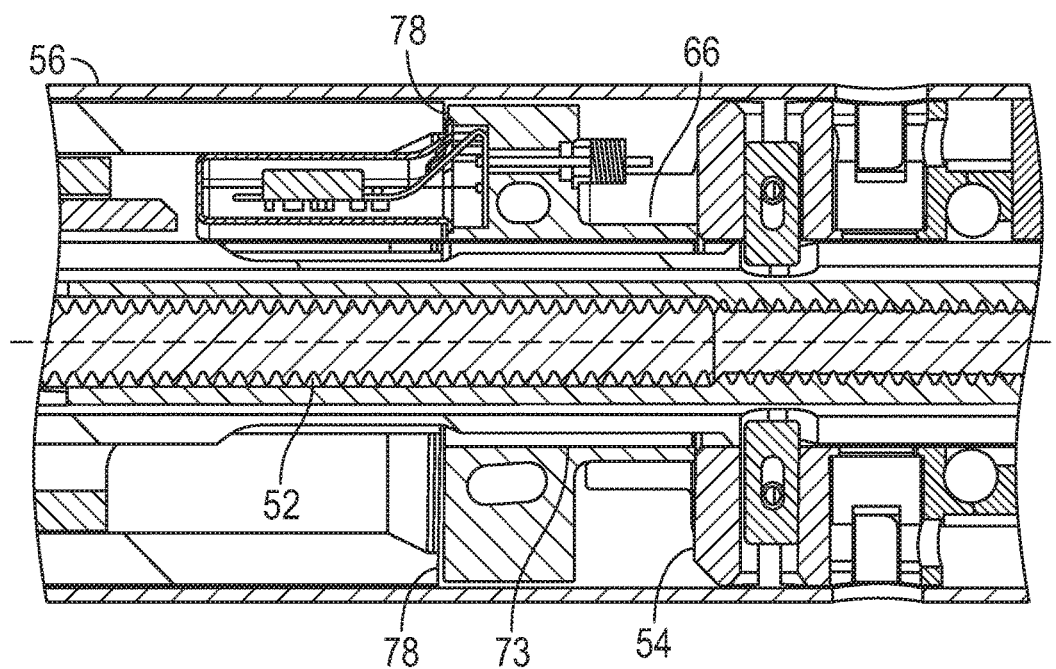
FIG. 6B is a cross-sectional view of the distal end portion of the adapter assembly according to an embodiment of the present disclosure.
Figure 7:
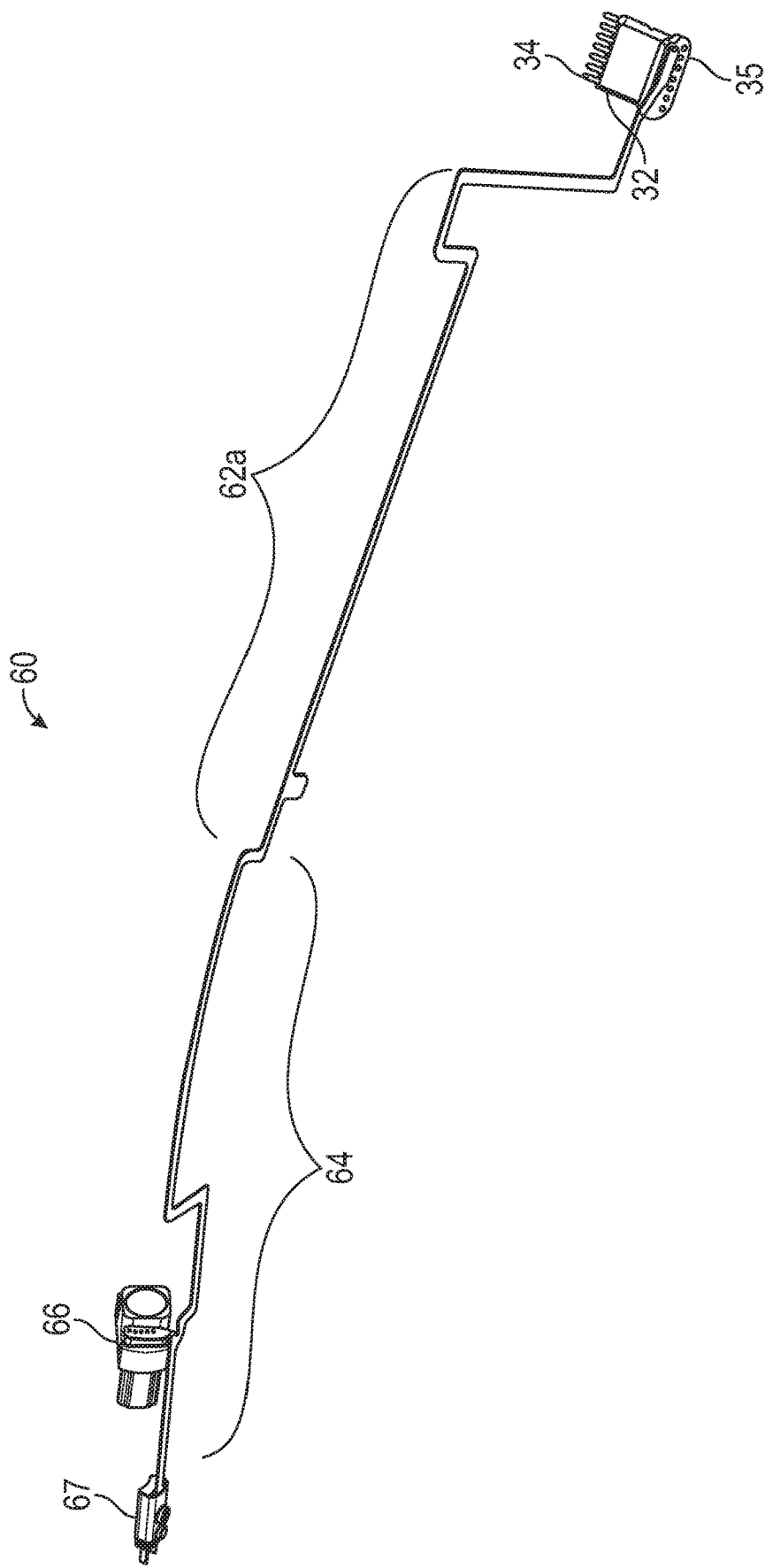
FIG. 7 is a perspective view of an electrical assembly of the adapter assembly of FIG. 1 according to an embodiment of the present disclosure.
Figure 8:
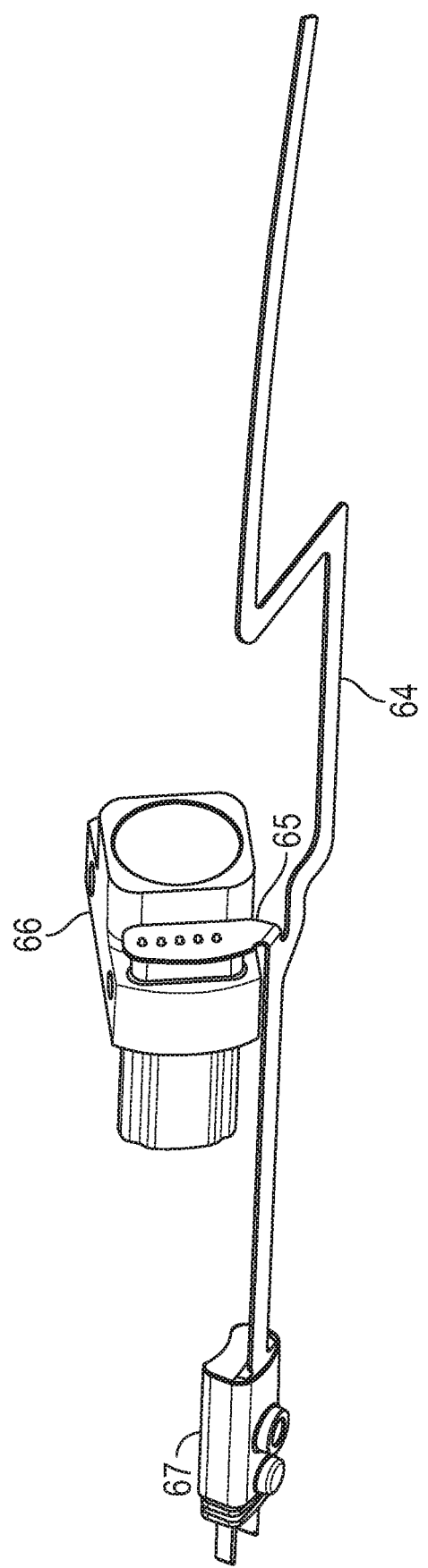
FIG. 8 is a perspective view of a distal portion of the electrical assembly according of FIG. 7 to an embodiment of the present disclosure.
Figure 9:
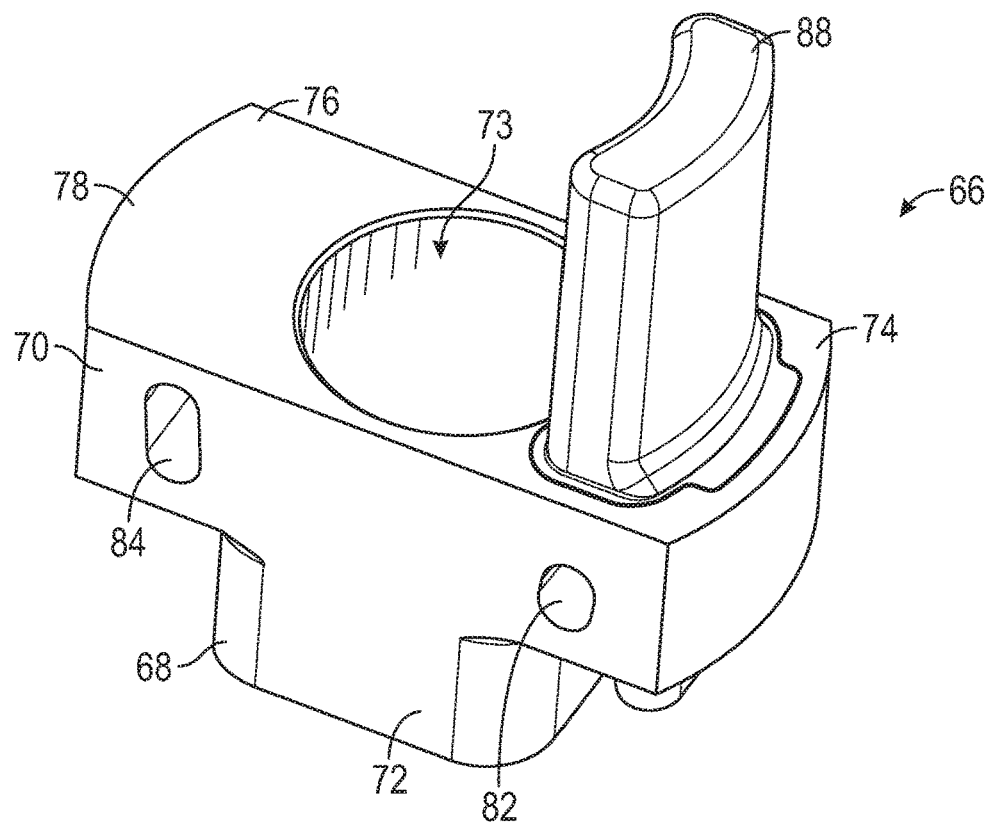
FIG. 9 is a perspective top view of a load sensing assembly of the electrical assembly of FIG. 7 according to an embodiment the present disclosure.
Figure 10:
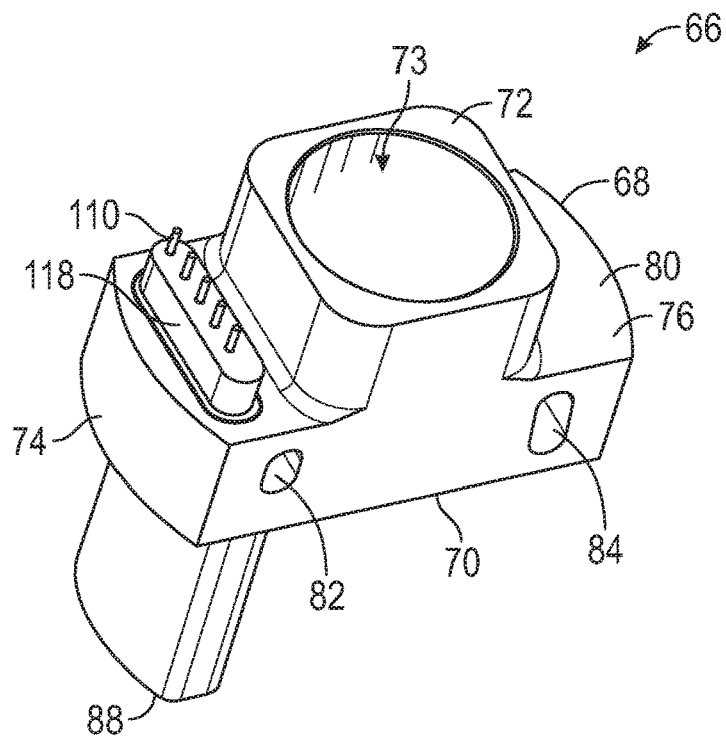
FIG. 10 is a perspective bottom view of the load sensing assembly of FIG. 9.

With reference now to FIGS. 6-8, adapter assembly 30 includes an electrical assembly 60 disposed therewithin, and configured for electrical connection with and between handle assembly 20 and reload 40. Electrical assembly 60 provides for communication (e.g., identifying data, lifecycle data, system data, load sense signals) with the main controller 38 of the handle assembly 20 through the electrical receptacle 29.

Electrical assembly 60 includes the electrical connector 32, a proximal harness assembly 62 having a ribbon cable, a distal harness assembly 64 having a ribbon cable, a load sensing assembly 66, and a distal electrical connector 67. The electrical assembly 60 also includes the distal electrical connector 67 which is configured to selectively mechanically and electrically connect to a chip assembly (not shown) of reload 40.

Electrical connector 32 of electrical assembly 60 is supported within the proximal end portion 30b of the adapter assembly 30. Electrical connector 32 includes the electrical contacts 34 which enable electrical connection to the handle assembly 20. Proximal harness assembly 62 is electrically connected to the electrical connector 32 disposed on a printed circuit board 35.

Load sensing assembly 66 is electrically connected to electrical connector 32 via proximal and distal harness assemblies 62, 64. Load sensing assembly is also electrically connected to distal harness assembly 64 via a sensor flex cable. As shown in FIGS. 6A and 6B, an actuation assembly 52, which is coupled to the trocar member 50, extends through the load sensing assembly 66. The load sensing assembly 66 provides strain measurements imparted on the adapter assembly 30 during movement of the trocar member 50 when coupled to the anvil assembly 58 during clamping, stapling, cutting, and other mechanical actuations.

For a detailed description of an exemplary powered surgical stapler including an adapter assembly and a reload, reference may be made to commonly owned U.S. Patent Application Publication No. 2016/0310134 to Contini et al., titled "Handheld Electromechanical Surgical System," filed Apr. 12, 2016, incorporated by reference hereinabove.

With reference to FIGS. 9-13, the load sensing assembly 66 includes a sensor body 68 having a platform 70 and a tubular portion 72 extending from the platform 70. The sensor body 68 also defines a lumen 73 through the platform 70, thereby separating the platform 70 into a first portion 74 and a second portion 76. The lumen 73 allows for the passage of the actuation assembly 52 therethrough. The sensor body 68 may be formed from any suitable material, such as stainless steel, that allows for the sensor body 68 to be elastically deformed when stressed. In embodiments, the sensor body 68 may be fabricated from stainless steel, such as 17-4 stainless steel heat-treated to H-900 standard.

The platform 70 also includes a top surface 78 and a bottom surface 80 (FIG. 10) as well as a first slot 82 defined within the first portion 74 of the platform 70 and a second slot 84 defined through the second portion 76 of the platform 70. Slots 82 and 84 work in combination with the design of sensor body 68 to provide uniform bending when loaded. The uniform loading and resulting strain output causes a load sensor circuit 86 (FIGS. 11 and 12) of the load sensing assembly 66 to provide provides linear strain output at the first portion 74 of the platform 70, which is measured by a load sensor circuit 86 secured to the first portion 74 and covered by a cover 88 as shown in FIG. 11.

With reference to FIGS. 6A and 6B, the load sensing assembly 66 is disposed between a support block 54 and a connector sleeve 56. In particular, the tubular portion 72 of the sensor body 68 rests on the support block 54 and the top surface 78 of the platform 70 abuts a proximal end of the connector sleeve 56. During operation of the surgical device 10, namely, clamping, stapling, and cutting, the sensor body 68 is elastically deformed (similar to a support beam) in proportion to the forces applied to the support block 54 and the connector sleeve 56. In particular, deflection of the sensor body 68 applies a force to the load sensor circuit 86 (FIGS. 11 and 12), which is deformed causing its electrical resistance to increase, which is reflected in its measurement signal. A change in a baseline of the measurement signal is indicative of the forces being imparted on the support block 54 and the connector sleeve 56, which are generally descriptive of the forces encountered during clamping, stapling, and cutting.

Figure 11:
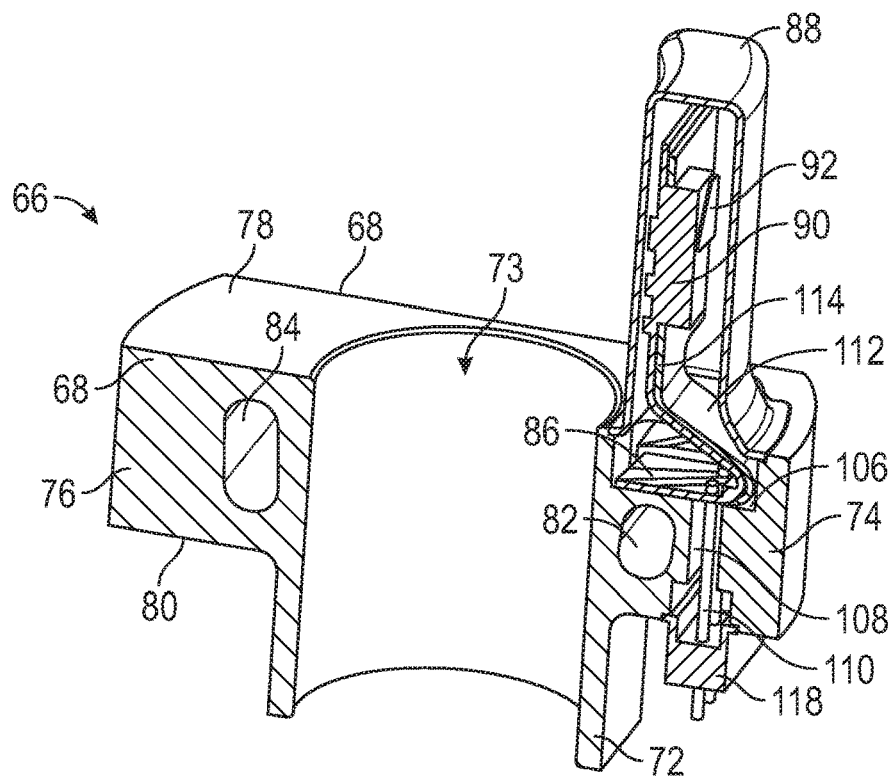
FIG. 11 is a cross-sectional, side view of the load sensing assembly of FIG. 9.
Figure 12:
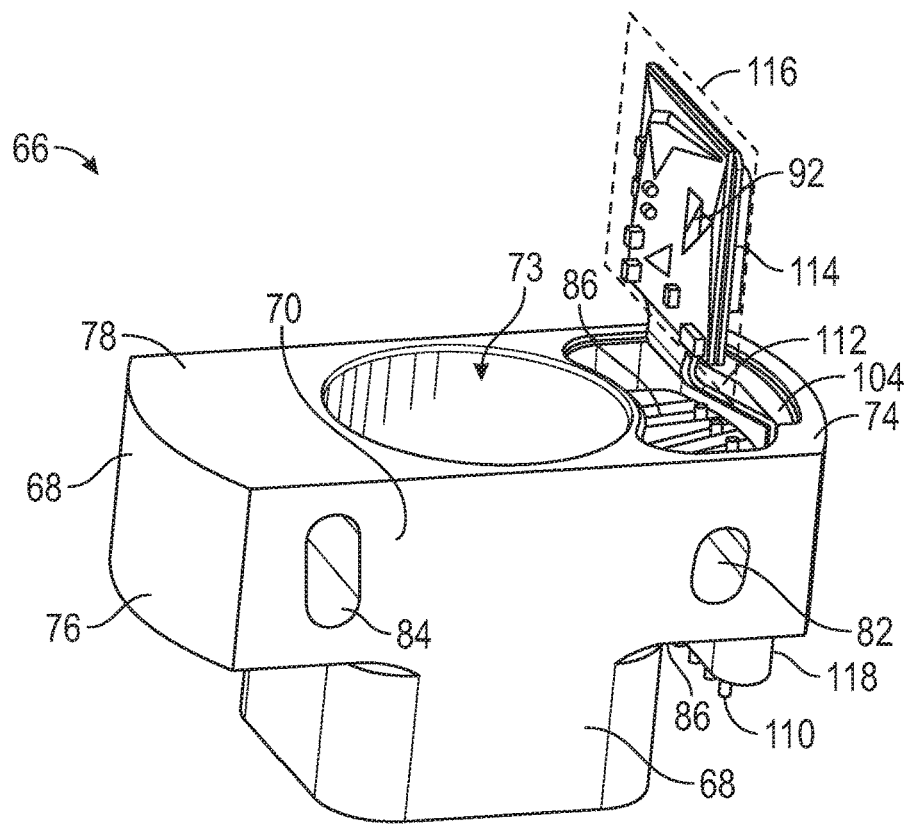
FIG. 12 is a perspective top view of the load sensing assembly of FIG. 8 without a cover.
Figure 18:
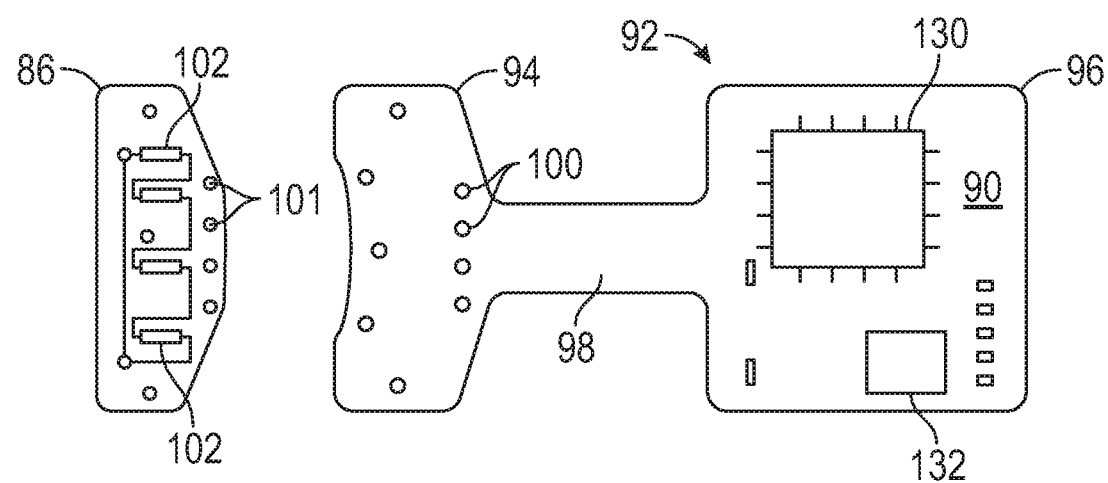
FIG. 18 is a top, schematic view of a load sensor circuit and a signal processing circuit according to an embodiment the present disclosure.

With reference to FIGS. 11, 12, and 18, the load sensor circuit 86 is coupled to a signal processing circuit 90, which includes a flexible circuit board 92 having a contact portion 94 and a signal processing circuit portion 96. The contact portion 94 is interconnected with the signal processing circuit portion 96 via a flex strip 98 and includes a plurality of first pass-through contacts 100. The signal processing circuit 90 includes analog and digital circuit components (e.g., controller 130) that are configured to perform signal processing on signals from the load sensor circuit 86 and output a measurement signal to the handle assembly 20.

The flexible circuit board 92 may be any suitable dielectric multilayer flexible materials, such as PYRALUX® materials available from DuPont of Willmington, Del., liquid crystal polymer materials, and the like. In embodiments, the flexible circuit board 92 may include additional dielectric layers, which stiffen the flexible circuit board 92 so that the solder connections of the components located along the flexible circuit board 92 are not subjected to unwanted movement due to thermal expansion and/or mechanical movement of the load sensing assembly 66. In embodiments, the flexible circuit board 92 may fabricated in a flat state (FIG. 18) and formed during soldering to sensor body 68 (FIG. 11). In further embodiments, the flexible circuit board 92 may be pre-bent using a fixture with or without heat to form the desired shape denoted in FIG. 11.

The contact portion 94 is configured to couple to the load sensor circuit 86, which includes one or more load sensing devices 102 interconnected by a plurality traces or other conductors. In embodiments, the load sensing devices 102 may be strain gauges, pressure sensors (e.g., pressure sensing film), or any other suitable transducer devices configured to measure mechanical forces and/or strain and output an electrical signal in response thereto. Signal output is achieved when the load sensing circuit 86 is bonded to the sensor body 68 such that the load sensing devices 102 are positioned in the respective areas of linear strain output when load sensing assembly 66 is elastically deformed.

The load sensor circuit 86 may be a single circuit board, such as a flexible circuit board with the load sensing devices 102 being disposed thereon and electrically interconnected via internal traces. The load sensing devices 102 are also electrically coupled via traces to a plurality of second pass-through contacts 101. In embodiments, the load sensing devices 102 may be attached to the first portion 74 of the platform 70 individually, rather than through the load sensor circuit 86 and then wired together to provide for electrical coupling.

The plurality of load sensing devices 102 may be arranged on the load sensor circuit 86 in a variety of configurations to achieve temperature compensation or other resistor networks, such as a Wheatstone Bridge in which two load sensing devices 102 are arranged to move in response to tension of the load sensing assembly 66 and two load sensing devices 102 are arranged to move in response to compression of the load sensing assembly 66. The configuration of four load sensing devices 102 as shown in FIG. 18 provides maximum signal output and temperature compensation and is known as a full bridge circuit.

Figure 13:
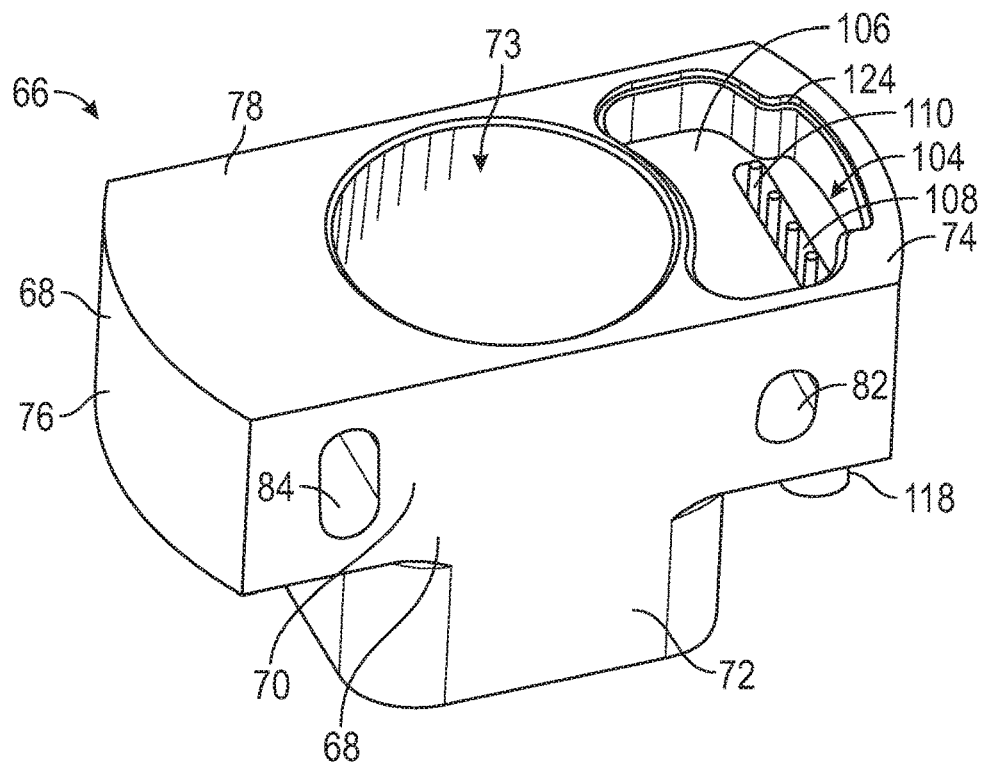
FIG. 13 is a perspective top view of the load sensing assembly of FIG. 8 without a load sensor circuit and a signal processing circuit.

With reference to FIG. 13, the first portion 74 also includes a pocket 104 having a gauging surface 106 for attachment of the load sensor circuit 86 and the contact portion 94 of the signal processing circuit 90. In embodiments, the load sensor circuit 86 may be bonded to the gauging surface 106 such that the signal processing circuit 90 outputs the measurement signal in response to the sensor body 68. The pocket 104 also includes a slot 108 having a plurality of pins 110 passing therethrough.

The slot 108 passes through the pocket 104 to the bottom surface 80 as shown in FIG. 11. The pins 110 are electrically coupled to the signal processing circuit 90 through a plurality of second pass-through contacts 101 (FIG. 18). In particular, when load sensor circuit 86 is bonded to the pocket 104, the second pass-through contacts 101 are inserted over pins 110. Thereafter the first pass-through contacts 100 of the contact portion 94 are also inserted over the pins 110. The first and second pass-through contacts 100 and 101 are aligned such that after soldering of the pins 110 thereto, the signal processing circuit 90 and the load sensor circuit 86 are electrically coupled to the pins 110 and each other. In embodiments, there may be four pins 110, with two of the pins 110 acting as communication lines and the remaining two pins 110 proving electrical power for energizing the load sensor circuit 86 and the signal processing circuit 90. After soldering, the flexible circuit board 92 can be arranged to fit within the cover 88.

In embodiments, the flexible circuit board 92 may be folded and/or bent as shown in FIGS. 11 and 12. In further embodiments, a support structure 112 may be disposed within the pocket 104. The support structure 112 includes one or more surfaces 114 onto which the flexible circuit board 92 is attached. The support structure 112 may have any suitable shape such that the flexible circuit board 92 is conformed to the shape of the support structure 112. The flexible circuit board 92 may be secured to the support structure 112 in any suitable manner, e.g., bonding, fasteners, etc.

In further embodiments, a wrap 116 can be disposed over the flexible circuit board 92 to insulate electronic components of the signal processing circuit portion 96 and prevent short circuits if the flexible circuit board 92 contacts an interior surface of the cover 88. The wrap 116 may be polyimide tape or ionomer resin tape, such as KAPTON® and SURLYN®, respectively, from DuPont of Wilmington, Del., shrink-wrap, polyisoprene membranes, low durometer potting compounds, parylene coatings, and other dielectric materials and applications suitable for insulating electronic circuits.

Figure 17:
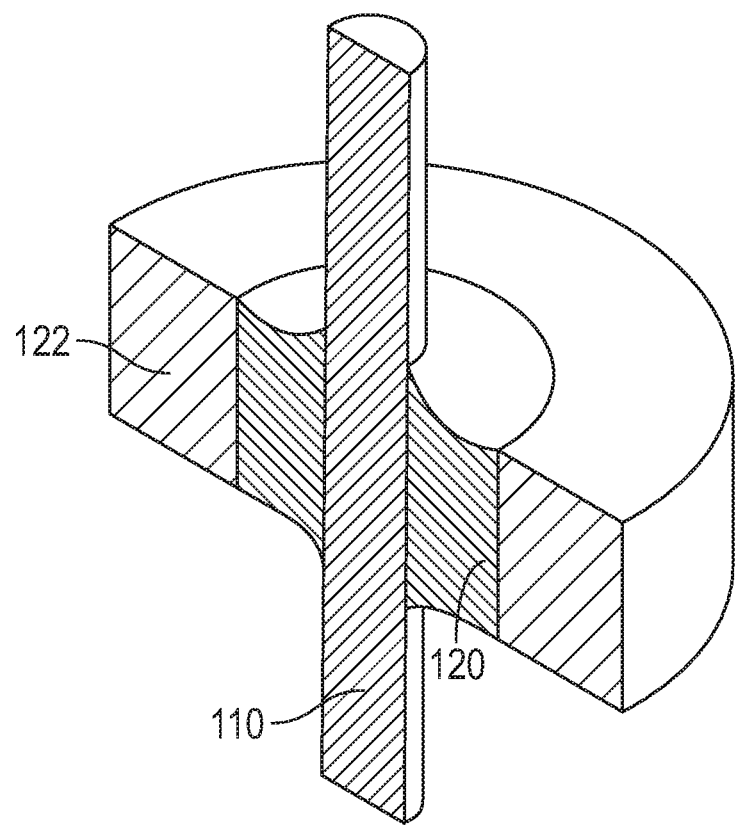
FIG. 17 is a cross-sectional view of a pin connector of the load sensing assembly of FIG. 9 according to an embodiment the present disclosure.

With reference to FIG. 10-13, the pins 110 are secured within a header 118, which hermetically seals the pocket 104 at the bottom surface 80. As shown in FIG. 17, each of the pins 110 is encased in a glass sleeve 120, each of which is then embedded in a peripheral housing 122. This construction seals the interior of cover 88 and the pocket 104 from the outside once the header 118 is bonded to slot 108 at the bottom surface 80 of the platform. The header 118 may be bonded (e.g., welded) to the bottom surface 80.

A hermetic seal may be formed by inserting the pins 110 through their respective glass sleeves 120, after which the pins 110 along with their glass sleeves 120 are inserted into corresponding bores of the peripheral housing 122 of the header 118. The entire assembly of the pins 110, glass sleeves 120, and the peripheral housing 122 are heated. Upon heating, the bore of the peripheral housing 122, which may be formed from any suitable metal (e.g., stainless steel), expands and the glass sleeves 120 fill the void. The pins 110 being formed from metal expand minimally and upon cooling, the glass sleeves 120 provide compression seals about their respective pins 110 and bores of the peripheral housing 122. As shown in FIG. 8, the pins 110 are the coupled to a flex cable 65, which in turn, is coupled to distal harness assembly 64.

Figure 14:
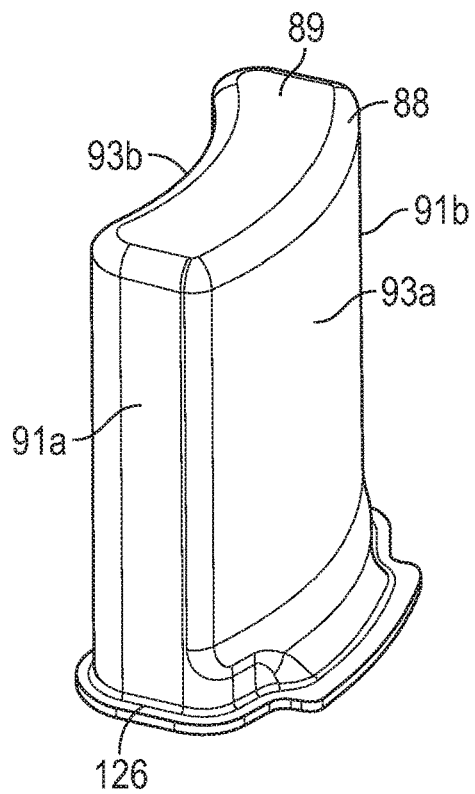
FIG. 14 is a perspective top view of a cover of the load sensing assembly of FIG. 9 according to an embodiment the present disclosure.
Figure 15:
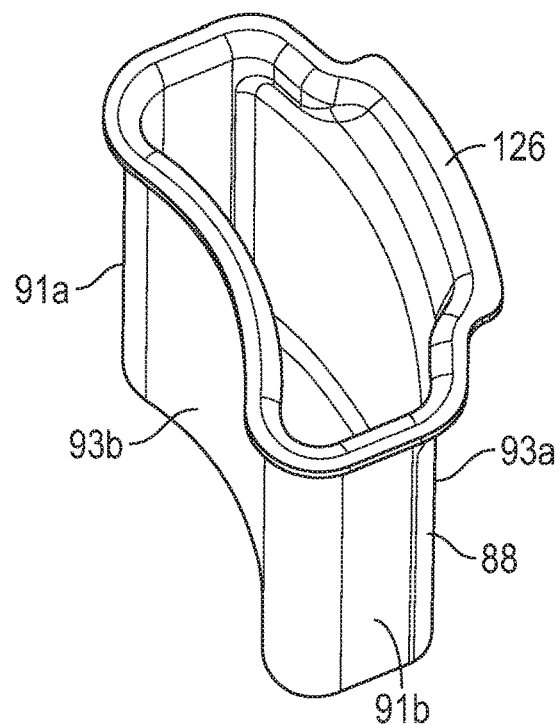
FIG. 15 is a perspective bottom view of the cover of FIG. 14.
Figure 16:
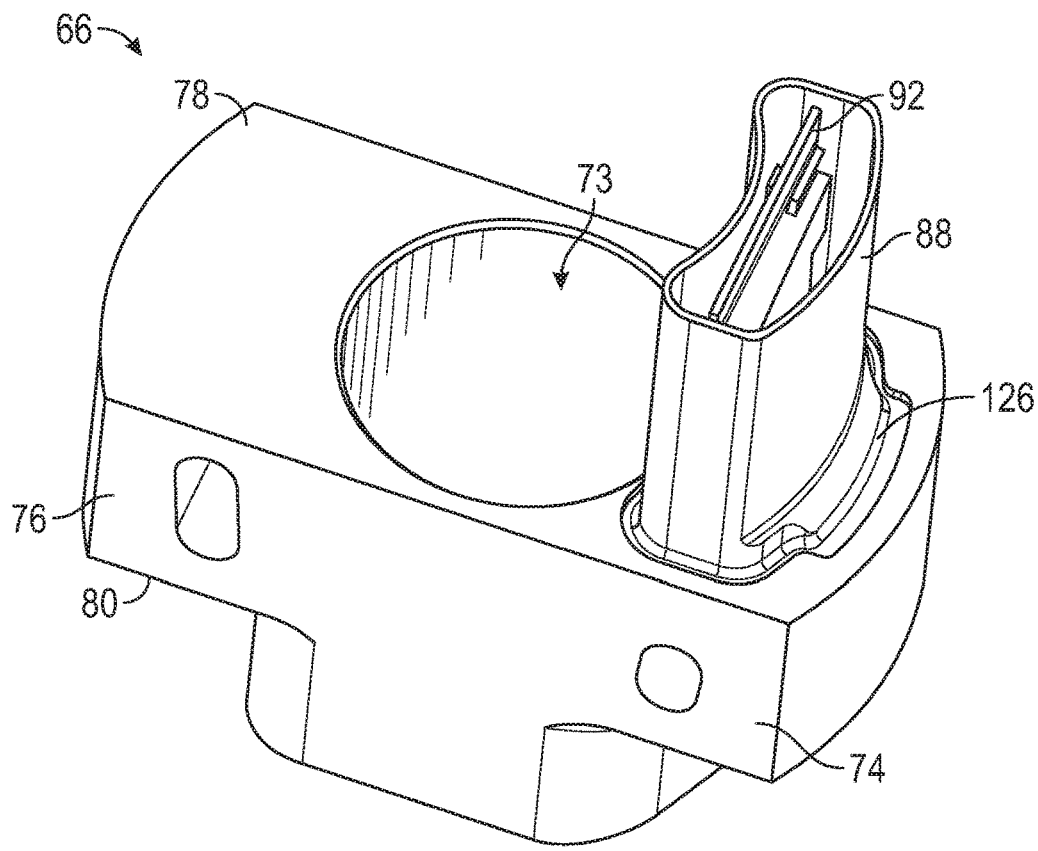
FIG. 16 is a perspective top view of the load sensing assembly of FIG. 9 with a partially cut-away view of the cover of FIG. 14 according to an embodiment the present disclosure.

With reference to FIG. 13, the pocket 104 further includes a step 124 along an entire perimeter of the pocket 104. The step 124 corresponds in size and shape to a flange 126 of the cover 88 as shown in FIGS. 14 and 15, to allow for creating of a hermetic seal. In addition, the flange 126 is configured to fit within the step 124 and is coplanar with the step 124. This allows for the flange 126 to sit on a flat surface portion of the step 124.

The cover 88 may be formed from a similar material as the sensor body 68. The cover 88 may be secured to the sensor body 68 in any suitable manner to ensure that the signal processing circuit 90 is hermetically sealed within the cover 88. In embodiments, the cover 88 and the sensor body 68 may be formed from a metal, such as stainless steel, and the cover 88 may be welded (e.g., by a laser) to the platform 70 around their respective perimeters. The cover 88 may be manufactured using a deep draw process, which provides for economical manufacturing. In embodiments, the sensor body 68 and the cover 88 may be manufactured using any suitable such as, machining, metal injection molding, 3-D printing, and the like.

With continued reference to FIGS. 14 and 15, the cover 88 includes a top wall 89, a pair of opposing side walls 91a and 91b, which are connected by a pair of opposing walls 93a and 93b. The walls 93a and 93b may have an arcuate shape to accommodate the signal processing circuit 90. In embodiments, the walls 89, 91a, 91b, 93a, 93b may have any suitable shape for enclosing the signal processing circuit 90. More specifically, the walls 89, 91a, 91b, 93a, 93b define an inner cavity 95, which fits over the signal processing circuit 90. The inner cavity 95 also encloses the signal processing circuit 90 in a thermal management material. In embodiments, the inner cavity 95 may be filled with the thermal management material such as by using pre-metered injectors. The signal processing circuit 90, which is attached to the sensor body 68, is then inserted into the filled inner cavity 95, after which the cover 88 is secured to the sensor body 68 as described above. After the cover 88 is secured, the thermal management material may flow within the cavity 95 and the pocket 104, which is in fluid communication with the cavity 95.

The thermal management material may be any liquid or semi-liquid (e.g., gel) dielectric material having high thermal conductivity. Viscosity of the thermal management material allows for ease of handling of the material. The high dielectric strength of the material electrically insulates the signal processing circuit 90 and electrical connections from the cover 88 and other conductive surfaces. The thermal conductivity allows for transfer of heat generated by the signal processing circuit 90 to the cover 88 and the sensor body 68. Since the cover 88 and the sensor body 68 may be metallic, which have high thermal conductivity as well, the cover 88 and the sensor body 68 act as heat sinks for the load sensor circuit 86 and the signal processing circuit 90, dissipating excess heat. The thermal management material also acts as a shock absorber by securing the load sensor circuit 86 and the signal processing circuit 90 within the inner cavity 95.

Thermal management material may include a grease component and a filler component. In embodiments, the grease component may be a dielectric grease or wax including a mineral oil, a petroleum oil, a synthetic oil such as glyceride or a silicone oil, which may include an organosiloxane, and combinations thereof. The filler component may be thermally-conductive filler particles, such as metal particles, metal oxide particles, metal nitride particles, metal carbide particles, metal diboride particles, graphite particles, and combinations thereof. Although the filler particles may be conductive, since the filler particles are dispersed through the thermal management material, there is no risk of short circuits. In further embodiments, the thermal management material may be semi-liquid or solid at normal room temperature, but may liquefy or soften at elevated temperatures to flow and better conform to the irregularities of the interface surfaces of the load sensor circuit 86 and the signal processing circuit 90.

Thermal management material may further include a fusible, e.g., low temperature melting, metal component. The fusible metal component may include one or more fusible metals, one or more fusible metal alloys, or a blend of one or more fusible metals and one or more fusible metal alloys. The fusible metal component may be form-stable at room temperature (25° C.) in a first phase, and conformable in a second phase, and having a transition temperature that is within the operating temperature range of the electronic components (e.g., the load sensor circuit 86 and the signal processing circuit 90) which may be from about 40° C. to about 100° C. Suitable fusible metals include bismuth, lead, tin, cadmium, indium, and combinations thereof. Suitable fusible metal alloys may include a fusible metal and one or more of the following metals: silver, zinc, copper, antimony. Addition of fusible metal components to the thermal management material allows the material to be self-supporting and form-stable at room temperature for ease of handling, while allowing the material to liquefy or otherwise soften at temperatures within the operating temperature range of the electronic components to form a viscous, thixotropic second phase which better conforms to the surfaces of electronic components within the cover 88.

Figure 19:
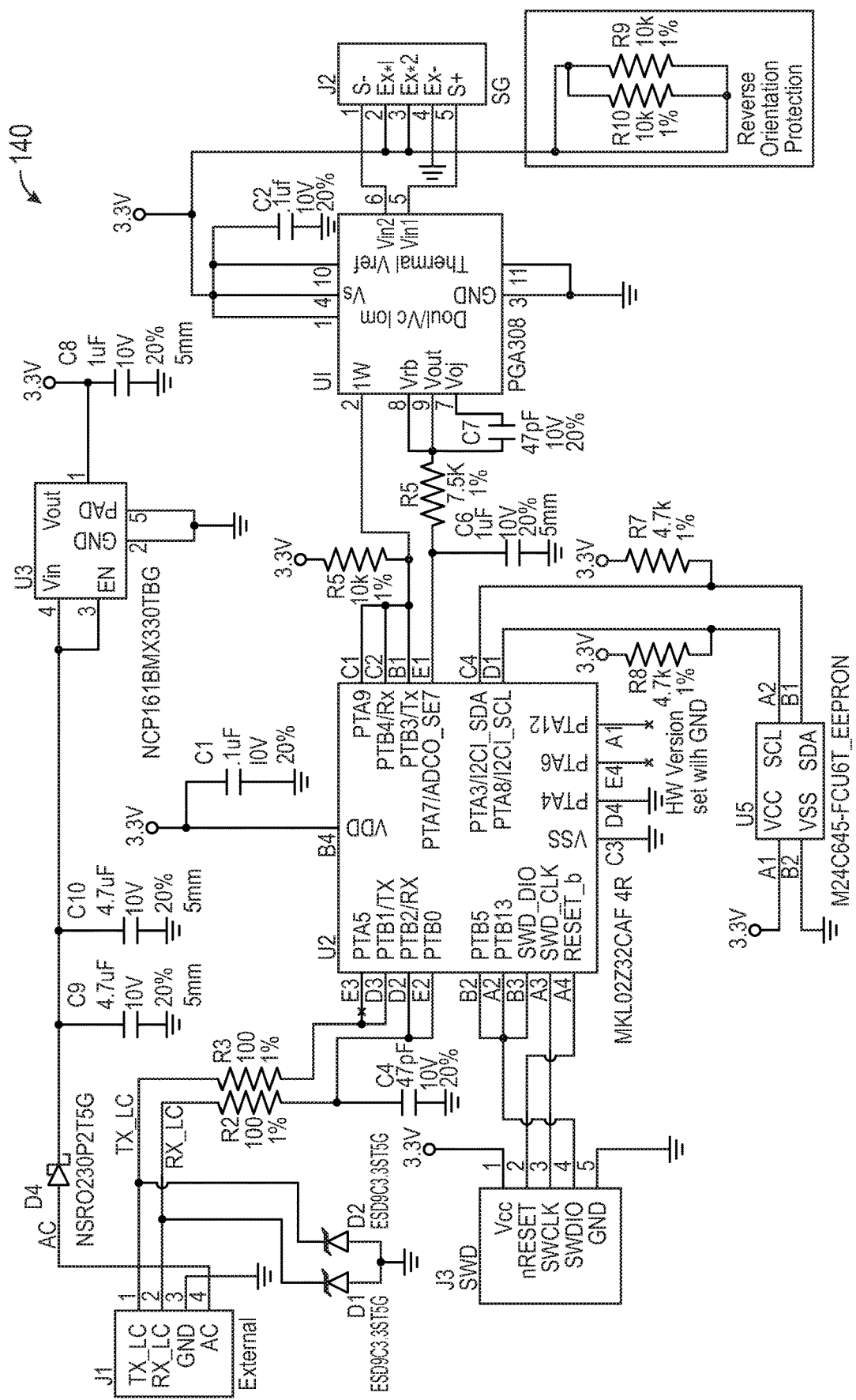
FIG. 19 is an electrical schematic drawing of the signal processing circuit of FIG. 18 according to an embodiment of the present disclosure.

With reference to FIGS. 18 and 19, the signal processing circuit 90 includes a controller 130 having a storage device 132, which may be an electrically erasable programmable read-only memory ("EEPROM") or any other suitable non-volatile memory device. The controller 130 may be any suitable microcontroller or any other processor, such as CORTEX® microcontrollers available from ARM of Cambridge, UK. The controller 130 may include analog-to-digital converters, digital-to-analog converters, timers, clocks, watchdog timers, and other functional components that enable the controller 130 to process the analog measurement signals from the load sensing devices 102. In particular, the controller 130 is configured to amplify the signal from the load sensing devices 102 of the load sensor circuit 86, filter the analog signal, and convert the analog signal to a digital signal. The controller 130 is also configured to transmit the digital signal to the main controller 38 of the handle assembly 20, which controls operation of the surgical device 10 based on the digital signal indicative of the sensed mechanical load.

The controller 130 is programmable to allow for adjustments to gain and offset parameters for processing the analog signal. In particular, the controller 130 stores a zero balance value and corresponding gain and offset parameters in the storage device 132. After assembly of the load sensing assembly 66, load sensor circuit 86 is calibrated. In embodiments, the load sensor circuit 86 may be recalibrated periodically to ensure accurate measurements. Calibration may be performed under zero balance, namely, when the load sensor circuit 86 is unloaded. If the load sensor circuit 86 is outputting any signal even in an unloaded state, or conversely, not outputting a sufficient signal in response to a loaded state, the controller 130 is programmed to compensate for such discrepancy. This is accomplished by adjusting gain and offset parameters of the controller 130, which allows the controller 130 to adjust the analog signal to correspond to the zero balance state. The controller 130 may be programmed through the main controller 38, which is coupled to the controller 130 through the pins 110 as described above.

It will be understood that various modifications may be made to the embodiments of the presently disclosed adapter assemblies. Therefore, the above description should not be construed as limiting, but merely as exemplifications of embodiments. Those skilled in the art will envision other modifications within the scope and spirit of the present disclosure.

What is claimed is:

1. A load sensing assembly comprising:
   a sensor body including a pocket defined therein;
   a load sensor circuit disposed within the pocket and coupled to the sensor body;
   a signal processing circuit disposed within the pocket and electrically coupled to the load sensor circuit;
   a cover defining a cavity and disposed over the pocket and enclosing the load sensor circuit and the signal processing circuit therein, the cover being coupled to the sensor body thereby forming a first hermetic seal therebetween; and
   a thermal management material disposed within the cavity and in contact with the load sensor circuit and the signal processing circuit.

2. The load sensing assembly according to claim 1, wherein the sensor body further includes a slot defined therein, the slot being connected to the pocket.

3. The load sensing assembly according to claim 2, further comprising a header including at least one pin coupled to the load sensor circuit and the signal processing circuit, wherein the header is coupled to the sensor body thereby forming a second hermetic seal therebetween.

4. The load sensing assembly according to claim 1, wherein the load sensor circuit includes at least one load sensing device.

5. The load sensing assembly according to claim 1, wherein the signal processing circuit includes a flexible circuit board having a dielectric wrap disposed over the flexible circuit board.

6. The load sensing assembly according to claim 1, wherein the thermal management material includes a grease component.

7. The load sensing assembly according to claim 6, wherein the grease component is selected from the group consisting of a mineral oil, a petroleum oil, and a synthetic oil.

8. The load sensing assembly according to claim 6, wherein the thermal management material includes a filler component.

9. The load sensing assembly according to claim 8, wherein the filler component is selected from the group consisting of metal particles, metal oxide particles, metal nitride particles, metal carbide particles, metal diboride particles, graphite particles, and combinations thereof.

10. The load sensing assembly according to claim 6, wherein the thermal management material includes a fusible metal component having a first phase at a first temperature and a second phase at a second temperature, which is higher than the first temperature.

11. The load sensing assembly according to claim 10, wherein the fusible metal component includes metal particles selected from the group consisting of bismuth, tin, lead, cadmium, and indium.

12. An adapter assembly comprising:
    a tubular housing having a proximal end portion and a distal end portion; and
    a load sensing assembly disposed with the tubular housing, the load sensing assembly configured to measure a load exerted on the tubular housing, the load sensing assembly including:
       a sensor body including a pocket defined therein;
       a load sensor circuit disposed within the pocket and coupled to the sensor body;
       a signal processing circuit disposed within the pocket and electrically coupled to the load sensor circuit;
       a cover defining a cavity and disposed over the pocket and enclosing the load sensor circuit and the signal processing circuit therein, the cover being coupled to the sensor body thereby forming a first hermetic seal therebetween; and
       a thermal management material disposed within the cavity and in contact with the load sensor circuit and the signal processing circuit.

13. The adapter assembly according to claim 12, wherein the thermal management material includes a grease component.

14. The adapter assembly according to claim 13, wherein the grease component is selected from the group consisting of a mineral oil, a petroleum oil, and a synthetic oil.

15. The adapter assembly according to claim 13, wherein the thermal management material includes a filler component selected from the group consisting of metal particles, metal oxide particles, metal nitride particles, metal carbide particles, metal diboride particles, graphite particles, and combinations thereof.

16. The adapter assembly according to claim 13, wherein the thermal management material includes a fusible metal component having a first phase at a first temperature and a second phase at a second temperature, which is higher than the first temperature.

17. The adapter assembly according to claim 16, wherein the fusible metal component includes metal particles selected from the group consisting of bismuth, tin, lead, cadmium, and indium.

18. A surgical device including:
    a handle assembly including a controller;
    an adapter assembly including:
       a tubular housing having a proximal end portion configured to couple to the handle assembly and a distal end portion; and
       a load sensing assembly disposed with the tubular housing, the load sensing assembly configured to measure a load exerted on the tubular housing, the load sensing assembly including:
          a sensor body including a pocket defined therein;
          a load sensor circuit disposed within the pocket and coupled to the sensor body;
          a signal processing circuit disposed within the pocket and electrically coupled to the load sensor circuit;
          a cover defining a cavity and disposed over the pocket and enclosing the load sensor circuit and the signal processing circuit therein, the cover being coupled to the sensor body thereby forming a first hermetic seal therebetween; and
          a thermal management material disposed within the cavity and in contact with the load sensor circuit and the signal processing circuit; and
    a surgical end effector configured to couple to the distal end portion of the adapter assembly.

19. The surgical device according to claim 18, wherein the thermal management material includes:

a grease component selected from the group consisting of a mineral oil, a petroleum oil, and a synthetic oil; and a filler component selected from the group consisting of metal particles, metal oxide particles, metal nitride particles, metal carbide particles, metal diboride particles, graphite particles, and combinations thereof.

20. The surgical device according to claim 18, wherein the thermal management material includes a fusible metal component having a first phase at a first temperature and a second phase at a second temperature, which is higher than the first temperature and the fusible metal component includes metal particles selected from the group consisting of bismuth, tin, lead, cadmium, and indium.

* * * * *